Figure 1:
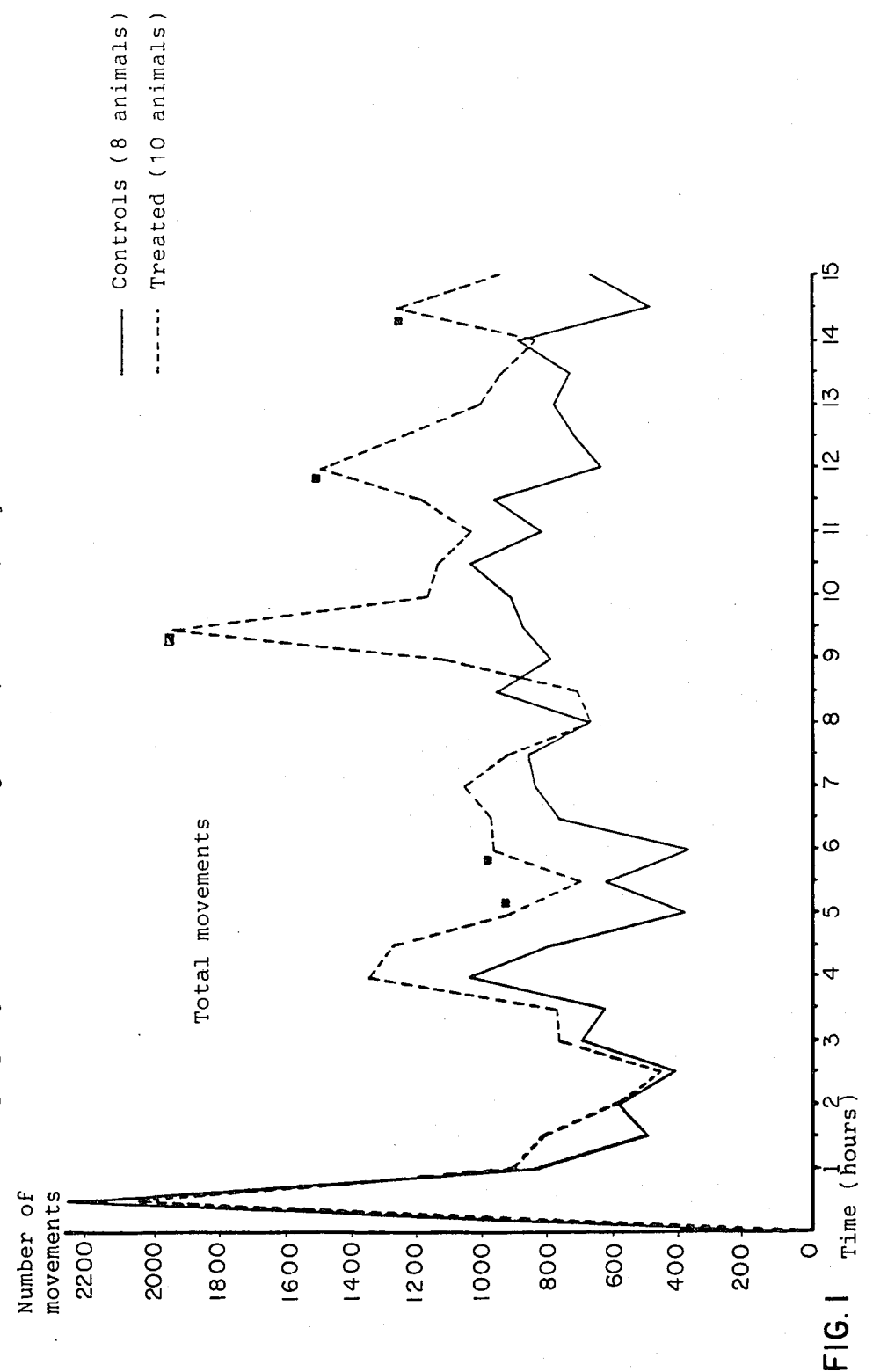
Figure 2:
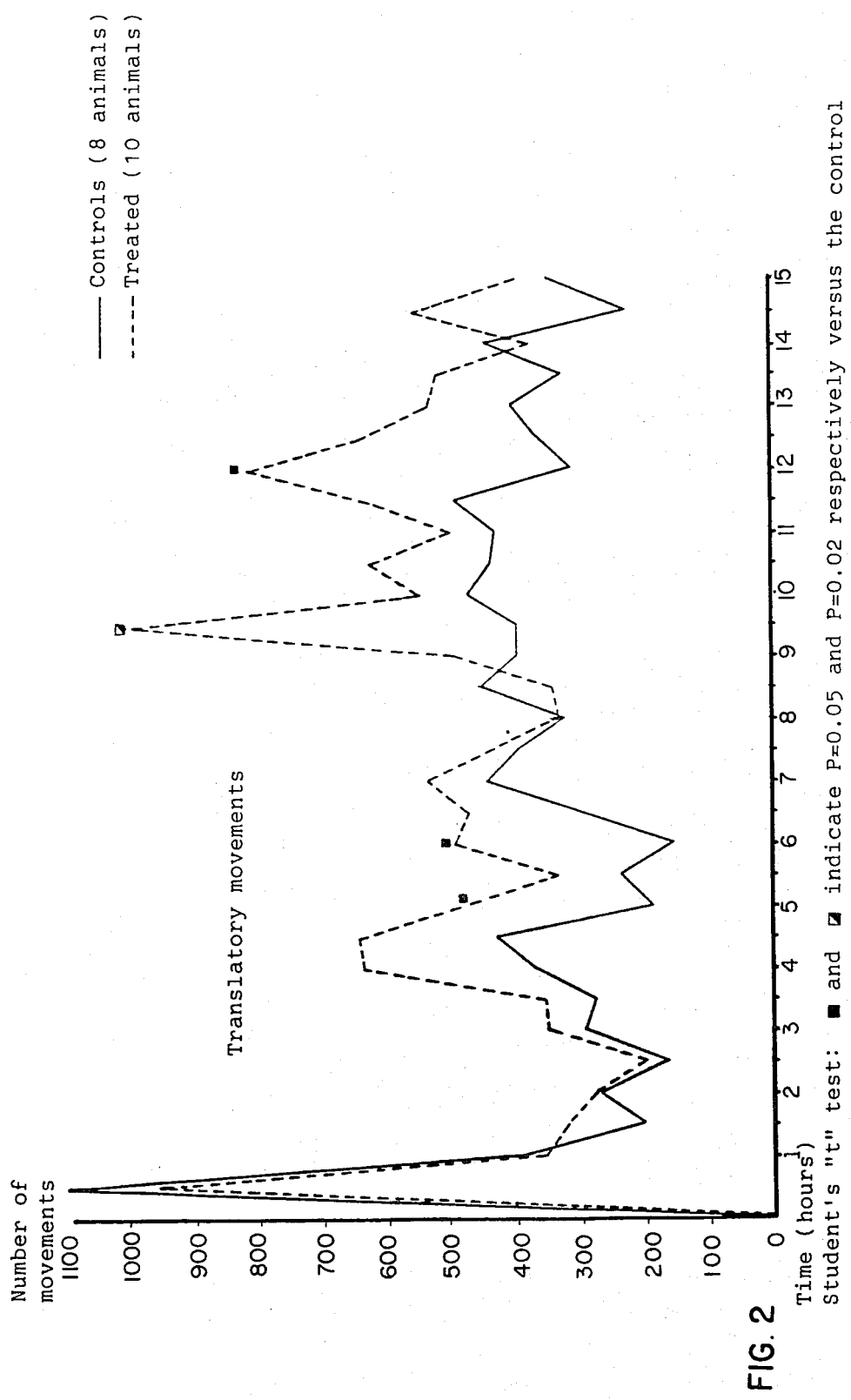
Figure 3:
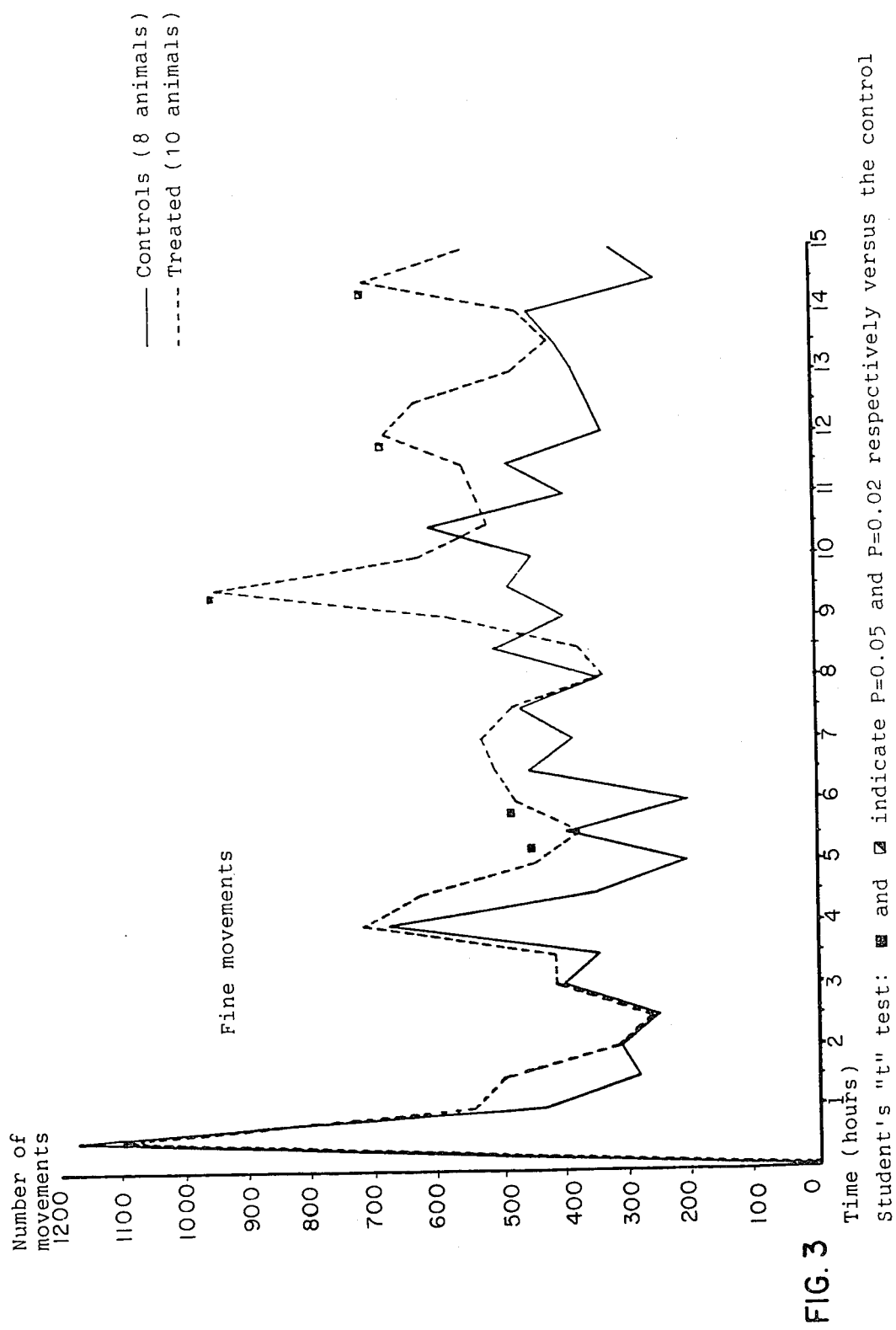
Figure 4:
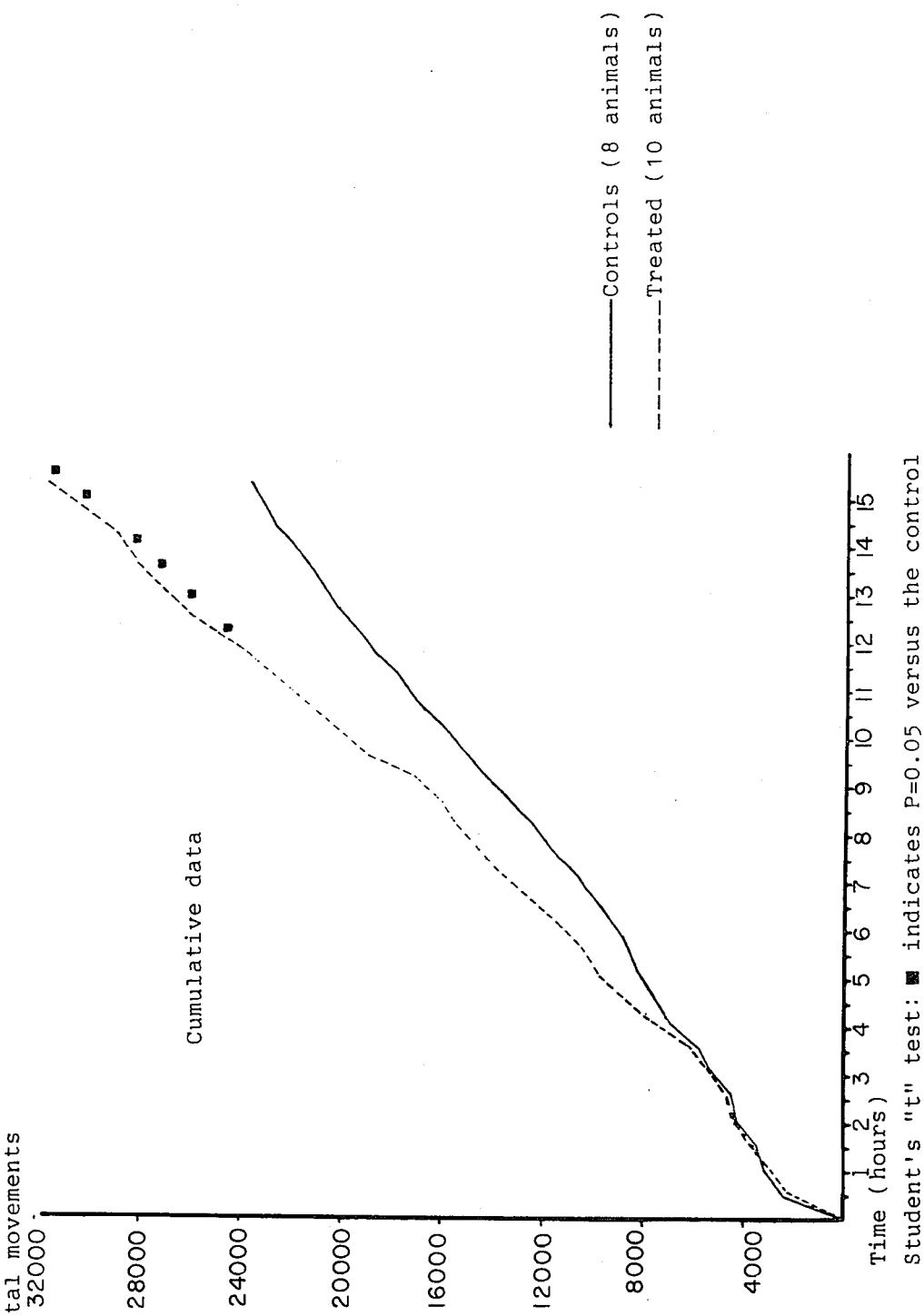
Figure 5:
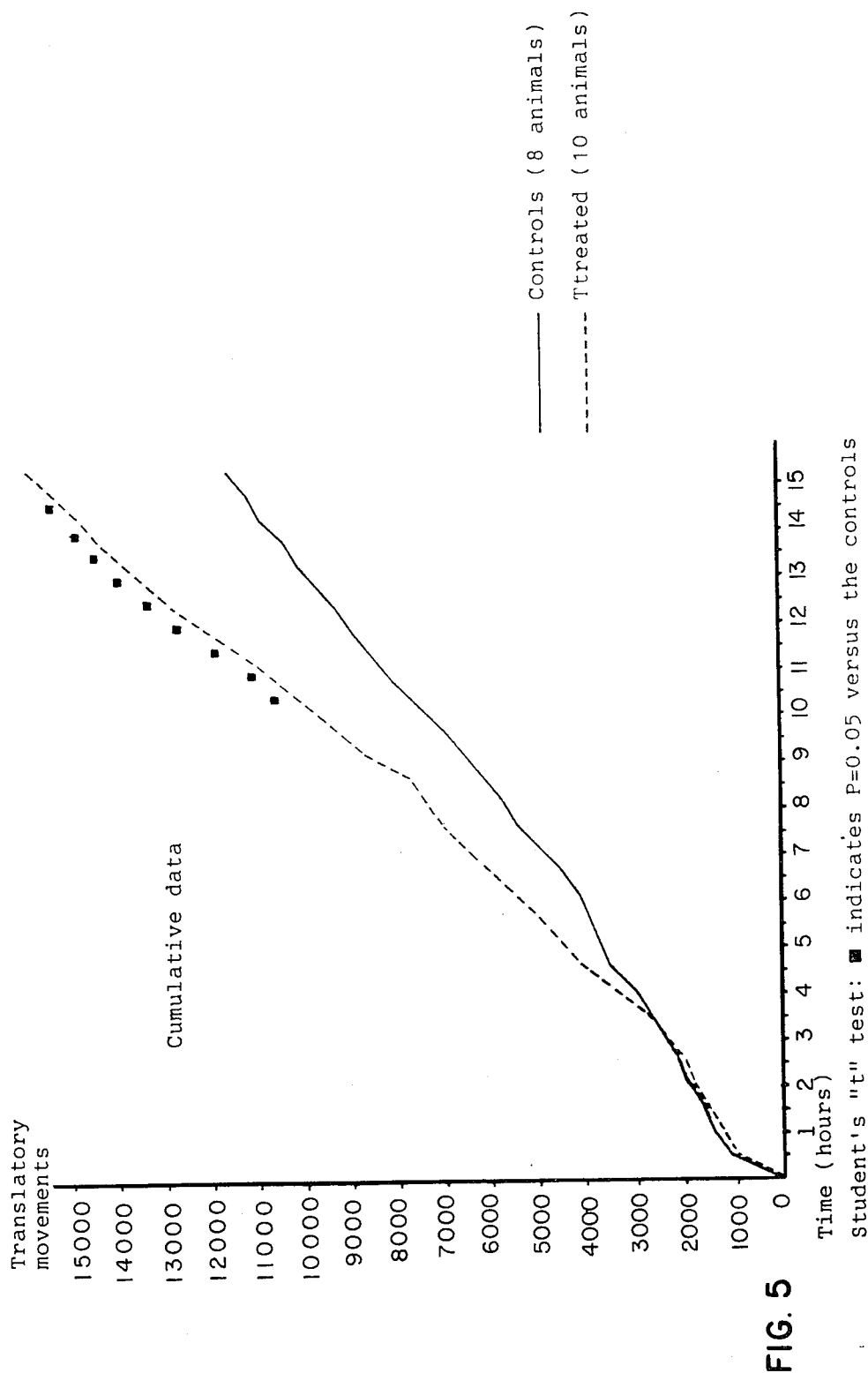
Figure 6:
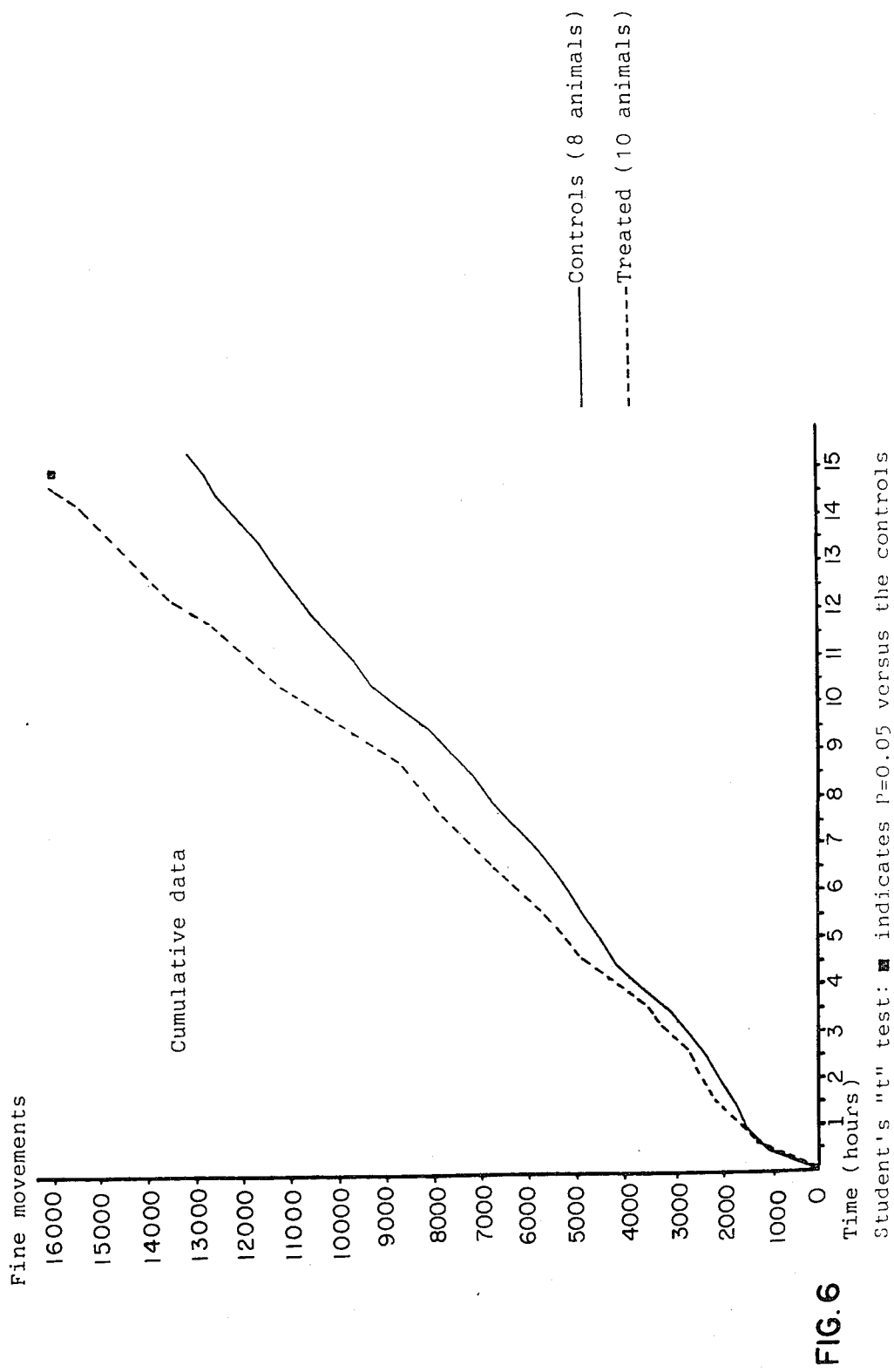

United States Patent [19]

Cavazza

[11] Patent Number: 4,474,812

[45] Date of Patent: Oct. 2, 1984

[54] PHARMACEUTICAL COMPOSITION FOR IMPROVING THE BIOCHEMICAL AND BEHAVIORAL PARAMETERS OF SENILITY

[75] Inventor: Claudio Cavazza, Rome, Italy

[73] Assignee: Sigma-Tau Industrie Farmaceutiche Riunite S.p.A., Rome, Italy

[21] Appl. No.: 545,141

[22] Filed: Oct. 25, 1983

[30] Foreign Application Priority Data

Oct. 29, 1982 [IT] Italy .................................. 49398 A/82

[51] Int. Cl.$^3$ ........................................... A61K 31/195
[52] U.S. Cl. ..................................................... 424/319
[58] Field of Search ......................................... 424/319

[56] References Cited

U.S. PATENT DOCUMENTS

| 4,267,163 | 5/1981 | De Felico | 424/319 |
| 4,315,944 | 2/1982 | Ramacci | 424/319 |
| 4,320,145 | 3/1982 | Cavazza | 424/319 |

Primary Examiner—Stanley J. Friedman
Attorney, Agent, or Firm—Bruce M. Collins

[57] ABSTRACT

A novel therapeutical use of L-carnitine and a pharmaceutical L-carnitine-comprising composition are disclosed, whose oral or parenteral administration to elderly subjects brings about an improvement in the biochemical and behavioral parameters peculiar to senility.

1 Claim, 6 Drawing Figures

PHARMACEUTICAL COMPOSITION FOR IMPROVING THE BIOCHEMICAL AND BEHAVIORAL PARAMETERS OF SENILITY

The present invention relates to a novel therapeutical use of L-carnitine and a pharmaceutical, orally or parenterally administrable, L-carnitine-comprising composition. Broadly, this novel use relates to the treatment of senility.

More specifically, this new use of L-carnitine relates to the improvement of the biochemical and behavioural parameters which are regarded as peculiar to senility.

Previous therapeutical uses of L-carnitine are already known. For instance, L-carnitine has been used in the cardiovascular field in the treatment of acute and chronic myocardial ischaemia, angina pectoris, cardiac arrhythmias and insufficiency. In nephrology, L-carnitine has been administered to chronic uraemic patients who are subjected to regular haemodialysis treatment with a view to counteracting muscular asthenia and the onset of muscular cramps. Further therapeutical uses are the restoration of the HDL/LDL+VLDL ratio to normal and in total parenteral nutrition.

There is no relationship at all, however, between the previously mentioned, known therapeutical uses of L-carnitine and the novel use which is the subject matter of the present invention.

It is, therefore, unexpected and surprising that, by orally or parenterally administering L-carnitine to elderly subjects, an improvement in the biochemical and behavioural parameters peculiar to senility, is brought about.

Although the daily dose to be administered depends on the age, weight and general condition of the elderly subject, utilizing sound professional judgment, it has been found that, generally, from about 10 to about 30 mg of L-carnitine/kg of body weight/day or an equivalent amount of a pharmacologically acceptable salt thereof, is a suitable dose.

L-carnitine is compounded into the pharmaceutical compositions by using the usual excipients, diluents and adjuvant agents which are well-known in pharmaceutical technology for preparing orally and parenterally administrable compositions. An extensive list of such excipients and adjuvant agents as well as the methods for preparing solid and liquid oral unit dosage forms such as tablets, capsules, solutions, syrups and the like and fluid injectable forms such as sterile solutions, is disclosed in the U.S. Pat. No. 3,830,931 to De Felice.

It has also been found that a pharmaceutical composition in unit dosage form which is particularly suited for the foregoing therapeutical uses comprises from about 500 to about 1,000 mg of L-carnitine.

Several experiments were carried out, some of which are hereinbelow described. The relevant results are also indicated.

Study of the effects of L-carnitine administration on some biochemical and behavioural parameters in old male rats A prolonged treatment of 105 days was carried out by administering L-carnitine to approximately 25-month old Albino Wistar rats, average body weight 500 grams. The animals were fed a normal diet. The treated animals were administered a dose of 50 mg of L-carnitine/kg/day; L-carnitine was dissolved in the drinking water. The controls received plain tap water. After 48 days of treatment 3 animals per group were sacrificed in order to make a first assessment of the L-carnitine content in serum and some organs. Between the 85th and 105th day of treatment, the motor activity test was performed on the surviving animals by placing them, one at the time, in the Animex device during night hours and recording the number of movements the animals made every 30 minutes for 15 hours starting from 5 p.m. During the test, the treated animals had free access to L-carnitine-containing drinking water. At the end of the 105 day-treatment, the rats were sacrificed and some serum and tissue biochemical parameters were studied. For the whole experiment duration the environmental conditions and the behavioural responses of the animals were monitored.

Results

Check after 105 days of treatment.

(1) MORTALITY

The animals were divided into two groups: controls (35 animals) and treated (34 animals) After 105 day-treatment, the following results were obtained:

| | |
|---|---|
| Controls | 20 dead animals |
| | 15 surviving animals |
| | Mortality rate: 57.1% |
| Treated | 10 dead animals |
| | 24 surviving animals |
| | Mortality rate: 29.4% |
| Fisher test | P = 2 |

(2) PERFORATED TABLE TEST (The holes explored by each animal in 30 minutes were recorded). In this test the following rats were employed:
10 young rats (4-month old)
10 untreated old rats (24-month old)
10 treated old rats (24-month old)
Results:

| | |
|---|---|
| young rats | 25 ± 2.8 |
| untreated old rats | 12 ± 3.3 |
| treated old rats | 21 ± 3.0 |
| Student's "t" | P ≦ 0.05 |

(3) MOTOR ACTIVITY

The motor activity of the L-carnitine treated rats was enhanced in a statistically significant way ($P < 0.05$) in comparison with the controls, in spite of the high variability detected among the individual cases.

Graphs 1, 2 and 3 which show the total movements, i.e. the translatory movements and the fine movements recorded each half an hour, illustrate that the most significant differences between controls and treated animals occurred between the 4th and the 6th hour and between the 9th and the 15th hour from test beginning.

Graphs 4, 5 and 6 show the cumulative values of the number of movements made every half an hour, which have been added to the previous movements.

The effect of carnitine is more evident on the translatory movements than on the other types of movements.

(4) STUDIES ON SOME ORGANS

Some organs (heart, liver, kidneys and tibial muscle) were excised from the sacrificed animals and the analyses suitable for elucidating the action mechanism of L-carnitine were carried out.

(a) Triglycerides in heart, liver and tibial muscle.
The results are illustrated in Table 1.

(b) Carnitine in heart, liver, kidney and tibial muscle.

The L-carnitine prolonged treatment brought about a significant increase of carnitine content in the heart and kidney of rats, even reaching values typical of young rats (see Table 2).

In the tibial muscle of the treated animals a non significant increase in L-carnitine was recorded.

(c) Carnitine Acetyl Transferase (CAT) and Carnitine Palmitoyl Transferase (CPT) in heart, liver, kidney and tibial muscle.

The results are summarized in Table 3.

(5) ISOLATED HEART

The reduction of L-carnitine particularly noticeable in the striated contractile structures, and the restoration to normal of L-carnitine levels in exogenous carnitine-administered rats with respect to young rats, led to investigate cardiac performances in control and treated, both young and old rats in order to have two control groups, old and young untreated rats.

(5.1) Coronary flow

L-carnitine treatment induced in any case a significant increase of coronary flow in young rats.

Old control rats showed statistically lower values than those of young control rats, whereas L-carnitine treatment brought about values comparable to those of young rats, even though a statistical significance did not appear between old control and treated rats. (see Table 4).

TABLE 1

Determination of triglycerides (mg/100 mg of tissue) in the heart, liver and tibial muscle of 25-month old male rats treated for 105 days with L-carnitine, 50 mg L-carnitine/kg/day in the drinking water

|  | Heart | Liver | Tibial muscle |
|---|---|---|---|
| Controls | 1.22 ± 0.15 (6) | 0.99 ± 0.13 (6) | 0.64 ± 0.10 (6) |
| Treated | 0.70 ± 0.12 (8) | 1.09 ± 0.16 (9) | 0.78 ± 0.10 (9) |

In parentheses the number of animals
Student's "t": $P \leq 0.01$

TABLE 4

Coronary flow (ml/min) in isolated heart of young and old rats, non-treated or L-carnitine treated (6 animals per group)

| Times | 10' | 20' | 30' | 40' | 50' | 60' |
|---|---|---|---|---|---|---|
| young control rats | | | | | | |
| $\bar{x} \pm$ s.e. | 22.0 ± 1.9 | 22.5 ± 1.5 | 22.5 ± 1.5 | 22.2 ± 1.6 | 21.8 ± 1.4 | 21.5 ± 1.6 |
| young treated rats | | | | | | |
| $\bar{x} \pm$ s.e. | 30.3 ± 2.3■ | 32.2 ± 1.2▲ | 31.8 ± 1.3▲ | 31.3 ± 1.1▲ | 29.8 ± 1.3● | 28.3 ± 0.6● |
| Δ % vs. y.c. | +37.7 | +43.1 | +41.3 | +41.0 | +36.7 | +31.6 |
| old control rats | | | | | | |
| $\bar{x} \pm$ s.e. | 17.8 ± 1.2 | 17.8 ± 1.2■ | 17.0 ± 1.0◪ | 16.7 ± 1.2■ | 16.5 ± 1.2◪ | 16.2 ± 1.3■ |
| Δ % vs. y.c. | −19.1 | −20.9 | −24.4 | −24.8 | −24.3 | −24.7 |
| old treated rats | | | | | | |
| $\bar{x} \pm$ s.e. | 22.5 ± 2.7 | 22.8 ± 2.8 | 22.8 ± 3.2 | 22.5 ± 3.1 | 22.7 ± 3.0 | 22.0 ± 3.2 |
| Δ % vs. y.c. | +2.3 | +1.3 | +1.3 | +1.4 | +4.1 | +2.3 |
| Δ % vs. o.c. | +26.4 | +28.1 | +34.1 | +34.7 | +37.6 | +35.8 |

Student's "t" test for differences versus young controls: ■ = $p \leq 0.05$; ◪ = $p \leq 0.02$; ● = $p \leq 0.01$ ▲ = $p \leq 0.001$ (5.2) Aortic flow

TABLE 2

Serum and tissue L-carnitine determination in 25-month old male rats treated for 105 day with L-carnitine, 50 mg L-carnitine/kg/day in the drinking water

|  | Serum μmoles/l | Heart nmoles/g | Liver nmoles/g | Kidney nmoles/g | Tibial muscle nmoles/g |
|---|---|---|---|---|---|
| Controls | 28.56 ± 2.12 (5) | 455.04 ± 17.5 (4) | 307.05 ± 31.98 (5) | 360.90 ± 34.06 (4) | 739.02 ± 57.47 (4) |
| Treated | 43.13 ± 4.56■ (8) | 586.03 ± 31.65◪ (6) | 253.47 ± 30.41 (8) | 572.43 ± 39.00△ (6) | 903.12 ± 59.1 (6) |

Student's "t" test in comparison with the controls: ■, ◪ and △ indicate P = 0.05, 0.02 and 0.01, respectively.
In parentheses the number of animals.

TABLE 3

Carnitine Acetyl Transferase (CAT) and Carnitine Palmitoyl Transferase (CPT) determination in some organs of 24-month old male rats treated for 110 days with L-carnitine, 50 mg L-carnitine/kg/day in the drinking water.
Values are expressed as M/min/mg of protein

|  | Heart | Liver | Kidney | Tibial muscle |
|---|---|---|---|---|
| | | CAT | | |
| Controls | 5.83 ± 0.68 (7) | 0.51 ± 0.05 (7) | 2.69 ± 0.24 (7) | 3.40 ± 0.45 (7) |
| Treated | 8.46 ± 0.76■ (8) | 1.27 ± 0.25◩ (8) | 3.26 ± 0.47 (8) | 3.87 ± 0.89 (8) |
| | | CPT | | |
| Controls | 5.41 ± 0.61 (7) | 0.47 ± 0.09 (7) | 1.22 ± 0.16 (6) | 1.09 ± 0.19 (6) |
| Treated | 7.46 ± 0.68■ (8) | 0.99 ± 0.14◩ (8) | 1.04 ± 0.21 (8) | 1.14 ± 0.37 (8) |

Student's "t" test in comparison with the controls: ■ and ◩ indicate P = 0.05 and P = 0.02, respectively.
parentheses the number of animals.

Following L-carnitine treatment, aortic flow (ml/minute) significantly varied both in young and old rats. It is important to point out that old control rats showed lower values than those recorded in young rats (about 40%); also in treated rats, the difference between young and old rats was significant, however lower (about 30%).

This shows that L-carnitine treatment allows a better haemodynamic performance of the left ventricle to be achieved. (see Table 5).

The heart of the treated rats showed better performance in comparison with the controls: the differences recorded appeared statistically significant at all the times considered up to 50 minutes for the young rats and 30 minutes for the old rats. (see Table 6).

TABLE 6

Cardiac output (ml/minute) in the isolated heart of young and old rats non-treated or L-carnitine treated (6 animals per group).

| Times | 10' | 20' | 30' | 40' | 50' | 60' |
|---|---|---|---|---|---|---|
| young control rats | | | | | | |
| $\bar{x} \pm$ s.e. | 83.0 ± 3.5 | 85.5 ± 3.5 | 85.5 ± 3.1 | 83.0 ± 4.9 | 80.8 ± 6.3 | 77.8 ± 7.7 |
| young treated rats | | | | | | |
| $\bar{x} \pm$ s.e. | 111.0 ± 2.8▲ | 114.2 ± 2.7▲ | 112.2 ± 2.9▲ | 106.3 ± 3.4• | 101.2 ± 4.2■ | 94.0 ± 5.8 |
| Δ % vs. y.c. | +33.7 | +33.6 | +31.2 | +28.1 | +25.2 | +20.8 |
| old control rats | | | | | | |
| $\bar{x} \pm$ s.e. | 47.2 ± 2.1▲ | 48.0 ± 2.0▲ | 47.5 ± 2.4▲ | 49.3 ± 2.2▲ | 47.7 ± 2.1▲ | 47.2 ± 2.3• |
| Δ % vs. y.c. | −43.1 | −43.9 | −44.4 | −40.6 | −41.0 | −39.3 |
| old treated rats | | | | | | |
| $\bar{x} \pm$ s.e. | 72.2 ± 6.0○ | 72.8 ± 6.8○ | 70.0 ± 8.8□ | 67.5 ± 8.8 | 66.3 ± 9.0 | 64.0 ± 9.3 |
| Δ % vs. y.c. | −13.0 | −14.9 | −18.1 | −18.7 | −17.9 | −17.7 |
| Δ % vs. o.c. | +53.0 | +51.7 | +47.4 | +36.9 | +39.0 | +35.6 |

Student's "t" test for differences versus young controls: ▲ = $p \leq 0.001$
Student's "t" test for differences versus old controls: □ = $p \leq 0.05$; $p \leq 0.01$
Student's "t" test for differences versus young controls: ■ = $p \leq 0.05$; • = $p \leq 0.01$; ▲ = $p \leq 0.001$ (5.4) Cardiac work Also this parameter (calculated using the formula: systolic pressure × cardiac output/wet weight of heart) showed a statistical significance between control-treated, young-old rats.

TABLE 5

Aortic flow (ml/min) in the isolated heart of young and old rats, non treated or L-carnitine (6 animals per group)

| Times | 10' | 20' | 30' | 40' | 50' | 60' |
|---|---|---|---|---|---|---|
| young control rats | | | | | | |
| $\bar{x} \pm$ s.e. | 61.0 ± 2.8 | 63.0 ± 2.9 | 63.0 ± 2.1 | 60.8 ± 3.7 | 59.0 ± 5.3 | 56.3 ± 6.6 |
| young treated rats | | | | | | |
| $\bar{x} \pm$ s.e. | 80.7 ± 3.6• | 82.0 ± 2.9▲ | 80.3 ± 2.9▲ | 75.0 ± 3.9■ | 71.3 ± 4.6 | 65.7 ± 5.7 |
| Δ % vs. y.c. | +32.3 | +30.2 | +27.5 | +23.4 | +20.8 | +16.7 |
| old control rats | | | | | | |
| $\bar{x} \pm$ s.e. | 29.3 ± 1.3▲ | 30.2 ± 1.3▲ | 30.5 ± 2.0▲ | 32.7 ± 1.5▲ | 31.2 ± 1.5▲ | 31.0 ± 1.8• |
| Δ % vs. y.c. | −52.0 | −52.1 | −51.6 | −46.2 | −47.1 | −44.9 |
| old treated rats | | | | | | |
| $\bar{x} \pm$ s.e. | 49.7 ± 3.9■▲ | 50.0 ± 4.4■○ | 47.2 ± 6.1■□ | 45.0 ± 6.4 | 43.7 ± 6.7 | 42.0 ± 6.7 |
| Δ % vs. y.c. | −18.5 | −20.6 | −25.1 | −26.0 | −26.0 | −25.4 |
| Δ % vs. o.c. | +69.6 | +65.7 | +54.8 | +37.6 | +40.1 | +35.5 |

Student's "t" test for differences versus young controls: ■ = $p \leq 0.05$; • = $p \leq 0.01$; ▲ = $p \leq 0.001$
Student's "t" test for differences versus old controls: □ = $p \leq 0.05$; $p \leq 0.01$; Δ = $p \leq 0.001$ (5.3) Cardiac output L-carnitine treatment appeared to allow for a better performance of the myocardium contractility. (see Table 7)

TABLE 7

Cardiac work (systolic pressure x cardiac output/wet weight of heart) in the isolated heart of old and young rats, non treated or L-carnitine treated (6 animals per group).

| Times | 10' | 20' | 30' | 40' | 50' | 60' |
|---|---|---|---|---|---|---|
| young control rats | | | | | | |
| $\bar{x} \pm$ s.e. | 6.18 ± 0.31 | 6.54 ± 0.32 | 6.40 ± 0.31 | 6.10 ± 0.46 | 5.83 ± 0.58 | 5.52 ± 0.67 |
| young treated rats | | | | | | |
| $\bar{x} \pm$ s.e. | 7.75 ± 0.17• | 7.88 ± 0.12• | 7.68 ± 0.14• | 7.25 ± 0.17■ | 6.59 ± 0.31 | 5.84 ± 0.48 |
| Δ % vs. y.c. | +25.4 | +22.2 | +20.0 | +18.9 | +13.0 | +5.8 |
| old control rats | | | | | | |
| $\bar{x} \pm$ s.e. | 2.65 ± 0.08▲ | 2.76 ± 0.08▲ | 2.69 ± 0.10▲ | 2.77 ± 0.10▲ | 2.61 ± 0.08▲ | 2.61 ± 0.09• |
| Δ % vs. y.c. | −57.1 | −57.2 | −58.0 | −54.6 | −55.2 | −52.7 |
| old treated rats | | | | | | |
| $\bar{x} \pm$ s.e. | 4.66 ± 0.41■○ | 4.71 ± 0.47■○ | 4.48 ± 0.62■□ | 4.27 ± 0.60■□ | 4.13 ± 0.62□ | 3.91 ± 0.65 |
| Δ % vs. y.c. | −24.6 | −27.0 | −30.0 | −30.0 | −29.2 | −29.2 |

TABLE 7-continued

Cardiac work (systolic pressure x cardiac output/wet weight of heart) in
the isolated heart of old and young rats, non treated or L-carnitine
treated (6 animals per group).

| Times | 10' | 20' | 30' | 40' | 50' | 60' |
|---|---|---|---|---|---|---|
| Δ % vs. o.c. | +75.8 | +70.7 | +66.5 | +54.2 | +58.2 | +49.8 |

Student's "t" test for differences versus young controls: ▨ = p ≦ 0.02; • = p ≦ 0.01; ▲ = p ≦ 0.001
Student's "t" test for differences versus old controls: □ = p ≦ 0.05; p ≦ 0.01;
Student's "t" test for differences versus young controls: ■ = p ≦ 0.05; • = p ≦ 0.01; ▲ = p ≦ 0.001
Student's "t" test for differences versus old controls: □ = p ≦ 0.05

What is claimed is:

1. The method of treating the deterioration in biochemical and behavioral parameters in a subject exhibiting clinical senility which comprises orally or parenterally administering thereto in a single or multiple does regimen from about 10 mg/kg of body weight to about 30 mg/kg of body weight per day of L-carnitine or a therapeutically equivalent amount of a pharmacologically acceptable salt thereof.

* * * * *